US008575339B2

(12) United States Patent
Cheng

(10) Patent No.: US 8,575,339 B2
(45) Date of Patent: Nov. 5, 2013

(54) DERIVATIVES OF ERLOTINIB

(76) Inventor: Xueheng Cheng, Libertyville, IL (US)

( * ) Notice: Subject to any disclaimer, the term of this patent is extended or adjusted under 35 U.S.C. 154(b) by 33 days.

(21) Appl. No.: 13/176,000

(22) Filed: Jul. 5, 2011

(65) Prior Publication Data

US 2013/0012528 A1     Jan. 10, 2013

(51) Int. Cl.
*C07D 239/70*     (2006.01)
(52) U.S. Cl.
USPC .......................................... 544/253
(58) Field of Classification Search
None
See application file for complete search history.

(56) References Cited

U.S. PATENT DOCUMENTS

| 5,747,498 A * | 5/1998 | Schnur et al. | 514/266.4 |
| 2008/0166358 A1 * | 7/2008 | Tung | 424/158.1 |

FOREIGN PATENT DOCUMENTS

WO    WO 9630347 A1 * 10/1996

OTHER PUBLICATIONS

Patani et al, Bioisometerism: A Rational Approach in Drug Design, 1996, Chem.Rev. 96, 3147-3176.*

* cited by examiner

*Primary Examiner* — James O Wilson
*Assistant Examiner* — Oluwafemi Masha
(74) *Attorney, Agent, or Firm* — Justin Lampel

(57) ABSTRACT

This invention relates to novel compounds and hydrochloric acid salts thereof. More specifically, this invention relates to novel compounds and hydrochloric acid salts thereof derived from erlotinib. This invention also provides compositions comprising one or more compounds of this invention and a carrier and the use of the disclosed compounds and compositions in methods of treating diseases and conditions that are beneficially treated by administering an epidermal growth factor receptor tyrosine kinase (EGFR) inhibitor, such as erlotinib.

1 Claim, 2 Drawing Sheets

DERIVATIVES OF ERLOTINIB

FIELD OF THE INVENTION

Compounds derived from erlotinib, pharmaceutical compositions containing derivatives of erlotinib, and methods of using the same are provided.

BACKGROUND OF THE INVENTION

Erlotinib, also known as Tarceva™, or N-(3-ethynylphenyl)-6,7-bis(2-methoxyethoxy)quinazolin-4-amine, is a reversible epidermal growth factor receptor tyrosine kinase (EGFR) inhibitor. Its main therapeutic use is in the treatment of cancer. See FDA label for Tarceva at http://www.accessdata.fda.gov/drugsatfda_docs/label/2010/021743s14s161b1.pdf. Erlotinib is currently approved for treatment of non-small cell lung cancer (NSCLC) and pancreatic cancer. Clinical trials are on-going to evaluate erlotinib for other cancer diseases. Despite the beneficial activities of erlotinib, there is a continuing need for new compounds to treat cancer and related conditions. It is desirable to discover novel derivatives thereof. Erlotinib is described in U.S. Pat. Nos. 5,747,498 and RE41065.

SUMMARY OF THE INVENTION

Compounds and hydrochloric acid salts thereof derived from erlotinib are provided. The compounds derived herein, or a mixture of compounds derived herein, and a carrier may be used in treating diseases and other conditions. More specifically, the diseases and other conditions may be treated by administering an epidermal growth factor receptor tyrosine kinase (EGFR) inhibitor, such as erlotinib.

DETAILED DESCRIPTION OF THE INVENTION

Figure 1:
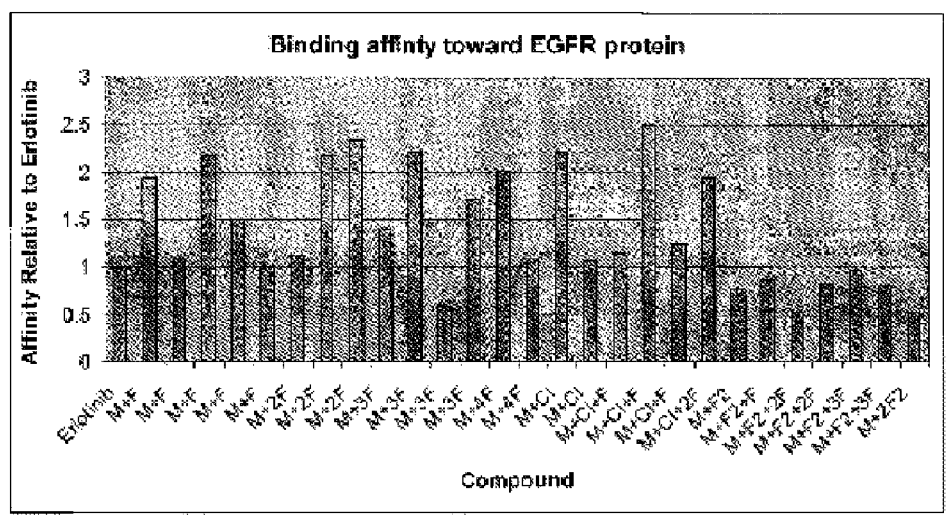
FIG. 1 depicts the affinity of selected compounds of the invention as compared to erlotinib in binding to EGFR protein.

Derivatives of erlotinib and compositions comprising derivatives of erlotinib are provided herein.

In one embodiment, the derivatives of erlotinib provide novel compounds of formula I-III or a pharmaceutically acceptable salt thereof, Formula I

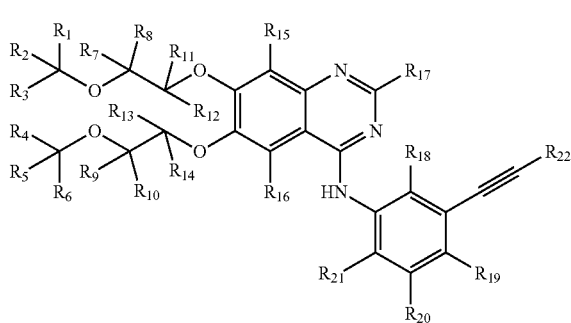

Formula II

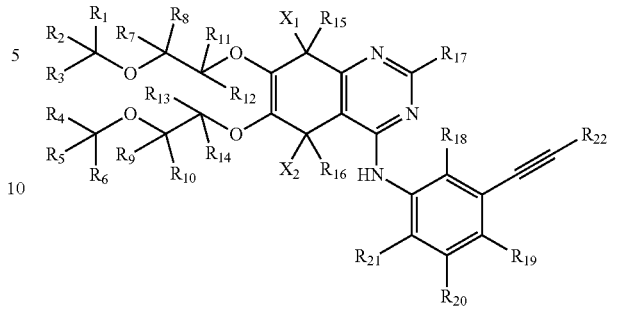

Formula III

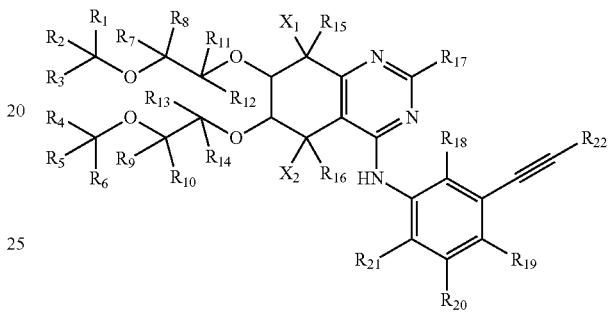

wherein R1-R22 and X1-X4 are independently selected from hydrogen, deuterium, methyl, lower alkyl, methoxy, lower alkoxy, aryloxy, trifluoromethyl, trifluoromethoxy, cyano, nitro, amino, lower alkylamino, lower dialkylamino, mercapto, lower alkylthio, arylthio, formyl, acetyl, lower alkylcarbonyl, arylcarbonyl, formate, lower alkylcarboxy, arylcarboxy, lower alkoxylcarboxy, aryloxylcarboxy, formamido, lower alkanoylamino, arylcarbonylamino, carbamido, lower alkylcarbamido, arylcarbamido, animocaboxy, lower alkylaminocarboxy, arylaminocarboxy, trifluoroacetyl, halogen, hydroxylcarbonyl, lower alkoxylcarbonyl, aryloxycarbonyl, solfinyl, lower alkylsolfinyl, arylsulfinyl, sulfonyl, lower alkylsulfonyl, arylsulfonyl, sulfonamido, lower alkylsulfonamido, arylsulfonamido, and aryl functional groups. At least one functional group among R1-R22 in formula I is not hydrogen.

In another embodiment, the derivatives of erlotinib provide novel compounds of formula I-III or a pharmaceutically acceptable salt thereof, wherein R1-R22 and X1-X4 are independently selected from hydrogen, fluorine, chlorine, or hydroxyl functional groups. At least one functional group among R1-R22 in formula I is not hydrogen.

In another embodiment, the derivatives of erlotinib provide novel pharmaceutical compositions, comprising a pharmaceutically acceptable carrier and a therapeutically effective amount of a compound of formula I-III.

In another embodiment, the derivatives of erlotinib provide a method for treating cancer comprising: administering to a patient in need thereof a therapeutically effective amount of compound of formula I-III.

In another embodiment, the derivatives of erlotinib may be used in therapy (e.g., for the treatment of cancer).

In another embodiment, the derivatives of erlotinib may be used for the manufacture of a medicament (e.g., for the treatment of cancer).

The present invention may be embodied in other specific forms without departing from the spirit or essential attributes thereof. It is understood that any and all embodiments of the invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

The compounds of formula I-III may have asymmetric centers. Compounds of formula I-III containing an asymmetrically substituted atom may be isolated in optically active or racemic forms. It is well known in the art how to prepare optically active forms, such as by resolution of racemic forms or by synthesis from optically active starting materials. All processes used to prepare compounds of formula I-III and intermediates made therein are considered to be part of the present invention. All tautomers, salts, hydrates, solvated forms of shown or described compounds are also considered to be part of the present invention.

Definitions. The examples provided in the definitions present in this application are non-inclusive unless otherwise stated. They include but are not limited to the recited examples.

Throughout this specification, a variable may be referred to generally (e.g., "each R" or "each X") or may be referred to specifically (e.g., R1, R2, R3, X1, X2, etc.). Unless otherwise indicated, when a variable is referred to generally, it is meant to include all specific embodiments of that particular variable.

The term "halogen" refers to any of —Cl, —F, —Br, or —I.
The term "carboxy" refers to —C(O)O—
The term "oxo" refers to =O.
The term "alkoxy" refers to —O-alkyl.
The term "alkylamino" refers to —NH-alkyl.
The term "dialkylamino" refers to —N(alkyl)-alkyl, wherein the two alkyl moieties are the same or different.

The term "alkyl" refers to straight or branched chains of carbon atoms, "lower alkyl" refers to straight or branched alkyl chains of from 1 to 12 carbon atoms, unless otherwise specified. Examples of straight chained and branched lower alkyl groups include methyl, ethyl, n-propyl, iso-propyl, n-butyl, sec-butyl, tert-butyl, pentyl, hexyl, pentyl and octyl. The alkyl group can contain substitution groups on the carbon chain.

The term "aryl" refers to optionally substituted carbocyclic aromatic groups such as phenyl and naphthyl. Suitable substituents on an aryl can include, but are not limited to for example, alkyl, halogen, cyano, hydroxyl, carboxy, alkoxy, amino, alkylamino and dialkylamino. The aryl group can contain one or more heteroatoms such as nitrogen, oxygen or sulfur in the ring.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. "Therapeutically effective amount" includes an amount of a compound of the present invention that is effective when administered alone or in combination to treat the desired condition or disorder.

"Pharmaceutically acceptable salts" refer to any non-toxic salt that, upon administration to a recipient, is capable of providing, either directly or indirectly, a compound of this invention. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluenesulfonic, naphthalenesulfonic, mandelic, and other acids.

The compounds of the present invention may be discovered by non-selective chemical modifications of erlotinib to form a derivative product mixture and identification of components of the derivative product mixture possessing unexpected improved properties. The novel compounds may be useful as therapies for the treatment of cancer.

Suitable methods were previously developed to generate non-selective chemical modification product mixtures from a compound of pharmaceutical utility and to screen the derivative product mixture to identify compounds possessing improved properties. Selected compounds can be purified from the derivative product mixture and their chemical identity can be determined by using chemical structure analysis techniques such as nuclear magnetic resonance (NMR) and mass spectrometry (MS). The previous techniques of non-selective chemical modification, preparation of derivative compound mixture (mixture compound libraries) and screening of the mixture compounds libraries for the discovery of compounds possessing improved properties were described in U.S. patent application Ser. No. 61/281,371 and Ser. No. 12/946,533, the contents of which are incorporated herein by reference.

The mixture compound libraries may be prepared from the reaction of erlotinib with elemental fluorine (in the form of mixture with high purity nitrogen) at a low temperature in an organic solvent. The mixture compound libraries may also be prepared with elemental fluorine and in the presence of a reagent that can donate a functional group during reaction with elemental fluorine. Generally, the reaction is performed in an inert organic solvent such as dichloromethane and acetonitrile.

Compounds of this invention may be obtained by chromatographic separation and purification using HPLC equipment from the mixture compound libraries. Separation can be done more than once to increase the purity of the compound so obtained.

After purification and structural determination, the compounds of this invention may also be prepared by organic synthesis methodologies that are within the knowledge of those skilled in the art of organic synthesis.

Formation of the salt form can be done by adding a corresponding acid to the free base compound solution in a suitable organic solvent, progressively reducing the amount of solvent. By working in this manner, the salt of the compound of this invention can be extracted from the mother liquors of crystallization by those skilled in the art of crystallization.

The present invention relates to pharmaceutical compositions containing one or more of pharmaceutically acceptable salts, in the pure state or in the presence of a diluent or a coating. These compositions may be employed orally or through other administration methods.

As solid compositions for oral administration, tablets, pills, powders or granules may be used. In these compositions, the active product according to the invention is mixed with one or more inert diluents such as sucrose, lactose or starch. These compositions can also comprise substances other than diluents, e.g. a lubricant or a component modulating the release, absorption or stability of the active product.

As liquid compositions for oral administration, solutions, suspensions, syrups, elixirs and pharmaceutically acceptable emulsions, containing inert diluents such as water or liquid paraffin, may be used. These compositions can also comprise substances other than diluents, e.g. wetting, sweetening or flavoring products.

Compositions can be a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The invention also provides a method of treating a disease that is beneficially treated by erlotinib in a patient in need thereof comprising the step of administering to said patient an effective amount of a compound or a composition of this invention.

In yet another aspect, the invention provides the use of a compound in a formulation alone or together with one or more additional therapeutic agents, either as a single composition or as separate dosage forms, for treatment or prevention in a patient of a disease, disorder or symptom set forth above.

For the discovery of erlotinib derivative compounds possessing unexpected improved properties, the following steps may be used.

Preparation of non-selective modification product mixtures of erlotinib (mixture compound libraries). 300 mg erlotinib was dissolved in 200 mL $CH_2Cl_2$ at $-78°$ C. cooled by dry-ice/acetone bath. A mixture of $F_2$ and $N_2$ gas containing 20% $F_2$/80% $N_2$ was passed through the reaction vessel continuously at a flow rate of 2 L/min. The reaction is stopped after 30 min and the solvent was removed under vacuum. Dried reaction products were dissolved in 20 mL acetonitrile and the solution was analyzed by LC-MS (Agilent 1200, Agilent Eclips 150×4.6 mm column, gradient elution from 10% acetonitrile/90% 0.1% formic acid in dd-$H_2O$ to 90% acetonitrile/10% 0.1% formic acid in dd-$H_2O$, 1 ml/min total flow rate, Waters LCT TOFMS in positive ion mode). Non-selective modification products may be distinguished based on HPLC retention time (RT) and molecular weight of the components.

Preparation of mixture derivative compounds for screening. Non-selective modification reaction product mixture of erlotinib was separated on an Agilent Zorbax C8 250×4.6 mm column, gradient elution from 30% MeOH/70% 0.1% formic acid in dd-$H_2O$ to 90% MeOH/10% 0.1% formic acid in dd-$H_2O$, 1 ml/min total flow rate. Each fraction was analyzed by LCT mass spectrometer. Some fractions may contain mostly the unreacted erlotinib, other fractions may contain various kinds of reaction products along with small amount of unreacted erlotinib. Those latter fractions may be mixed to form the modified erlotinib compound mixture (mixture compound library) for the subsequent screening.

Identification of compounds with improved properties. The identification of the compounds in the mixture compound library possessing improved properties can be done using procedures similar to that described in a previous invention (U.S. patent application No. 61/281,371 and Ser. No. 12/946,533, the contents of which are incorporated herein by reference). Specifically the mixture compound library may be screened, in a mixture format, for affinity toward the protein epidermal growth factor receptor tyrosine kinase (EGFR) using ultrafiltration, for metabolic stability using human liver microsome extraction, and for other pharmaceutical properties including, but not limited to: membrane permeability, plasma protein binding property, blood-brain-barrier (BBB) penetration property. Derivatives of erlotinib possessing improved properties over erlotinib itself may be detected from the above screening tests. The identity of the mixture compound library components may be specified as the retention time (RT) and m/z value in LC-MS analysis. Thus any components that are uniquely identified in LC-MS analysis as separate from other components based on retention time and m/z values can be monitored separately. For such "LC-MS separable" components, it can be determined whether one particular component has a better property or otherwise against the parent drug erlotinib by using LC-MS technique. Similarly NMR or other techniques can be used to determine pharmaceutical properties of the mixture components in the screening tests relative to the parent drug erlotinib itself. These mixture format screening tests and measurements by techniques such as LC-MS and NMR may allow detection and identification of components possessing improved properties relative to the parent drug erlotinib itself.

Affinity screening. Mixture compound library was mixed with a buffered solution containing 10 uM EGFR kinase enzyme at pH 7.4 (50 mM Tris HCl). The mixture was filtered through a ultrafiltration microcon filter (Millipore) with molecular weight cutoff (MWCO) of 10 kDa by centrifugation at 12000 rpm for 20 min. New buffer was added to the top of the filter and the solution was filtered through the microcon filter again. This process was repeated several times and a portion of the top layer of each filtration was removed and treated with organic solvent acetonitrile or methanol to denature the enzyme and to extract the erlotinib screening library compounds that bound to the enzyme. Compound concentration in the top layer was measured by LC-MS analysis (Agilent 1200, Agilent Eclips 150×4.6 mm, gradient elution from 10% acetonitrile/90% 0.1% formic acid in dd-$H_2O$ to 90% acetonitrile/10% 0.1% formic acid in dd-$H_2O$, 1 ml/min total flow rate, Waters LCT TOFMS in positive ion mode), and the relative affinity determined based on the concentration change after each round of filtering through microcon filter. A sample containing the erlotinib screening library but without the EGFR enzyme was treated the same way as the sample with EGFR enzyme to serve as a protein-negative control. The components with larger decrease in concentration in the sample with the EGFR enzyme after each filtering indicate lower affinity and vice versa. The affinity screening results allow identification of components of the non-selective modification product mixture that possess improved affinity toward EGFR protein relative to erlotinib itself. FIG. 1 depicts the affinity of selected compounds of the invention as compared to erlotinib in binding to EGFR protein.

Figure 2:
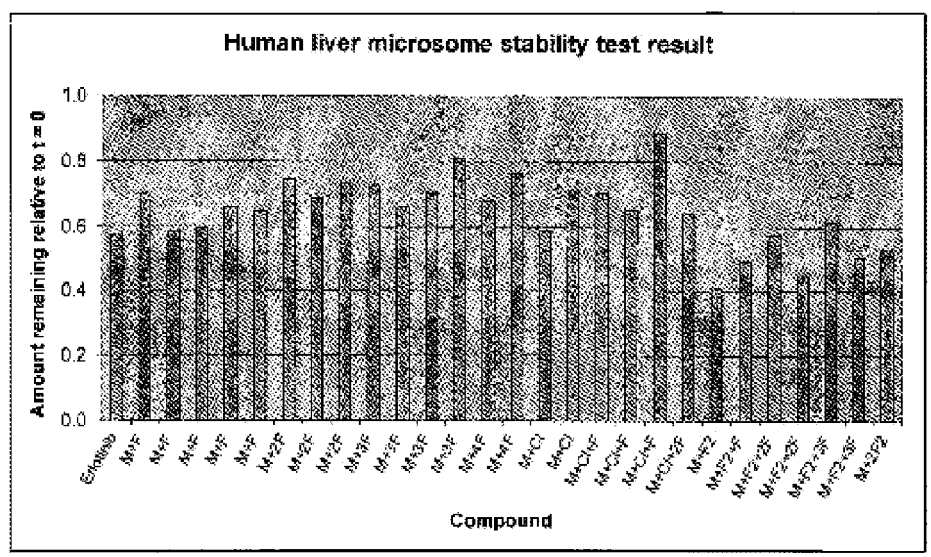
FIG. 2 depicts the metabolic stability of selected compounds of the invention as compared to erlotinib through incubation with human liver microsome.

Liver microsome stability testing. Mixture compound library was mixed with a buffered solution containing human liver microsome (Invitrogen Cat. No. HMMC-PL, 1 mg/mL diluted from 20 mg/mL stock with buffer), 1 mM NADPH in 50 mM KPO4, 3 mM MgCl2, pH7.4 for 2 hours at 37° C. and then was treated with 3 volumes of organic solvent acetonitrile to stop the metabolism reaction and to extract the screening library compounds. Control samples were also done where the mixture compound library was replaced by pure erlotinib and by positive reference compound terfenedine each at 1 uM. The concentration of compounds before and after the microsome incubation was measured by LC-MS analyses (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate, Waters LCT TOFMS in positive ion mode), and the relative metabolic stability determined based on the concentration change after incubation. The components with larger decrease in concentration after microsome incubation indicate lower metabolic stability and vice versa. The metabolic stability testing results allow identification of components of the non-selective modification product mixture that possess improved metabolic stability relative to erlotinib itself. FIG. 2 depicts the metabolic stability of selected compounds of the invention as compared to erlotinib through incubation with human liver microsome.

Isolation of compounds of interest. General isolation and purification methods can be used by those skilled in the art of compound isolation in medicinal chemistry or natural product chemistry. Specifically the compounds possessing improved properties relative to erlotinib can be isolated from the mixture compound library by using HPLC separation. A general procedure for isolating components from non-selective modification of erlotinib may be illustrated as below. The mixture may be separated first on an Agilent Eclips column such as 150×4.6 mm type, to be consistent with the analytical LC-MS used in the screening steps (Agilent 1200, Agilent Eclips 150×4.6 mm, gradient elution from 10% acetonitrile/90% 0.1% formic acid in dd-H2O to 90% acetonitrile/10% 0.1% formic acid in dd-H2O, 1 ml/min total flow rate). The mixture after such first separation may produce fractions that contain one particular compound as the major component and some other compounds as minor components. Those fractions that contain a compound of interest (such as the compound having improved properties relative to erlotinib) as major components may in turn be further purified by a second HPLC column of different type than Agilent Eclips, such as Supelco Discovery RP Amide C16 column (4.6×250 mm column, gradient 30%-90% MeOH/0.1% formic acid-ddH2O, 1 mL/min flow rate). Often after such second separation, the purity of the desired component will be sufficiently good for structure identification. Else the components of interest can be further separated by an HPLC column of a third type with different column chemistry than the one used in previous separations, such as a fluorine-based column (Thermo PFP Gold, 4.6×250 mm HPLC column, 80% MeOH/0.1% formic acid/20% H2O, isocratic separation, 1 mL/min flow rate). After separations, the compound of interest may be obtained as a major component with purify >90 of the fraction. Such purified compounds may then be used for structure determination and tested as individual, pure compound to confirm the improved properties over the parent drug erlotinib. Drug property tests may include, but not limited to: affinity toward epidermal growth factor receptor tyrosine kinase protein, metabolic stability using human liver microsome, and biological activity using enzyme assays and cellular activity assays.

Structural determination of compounds purified from the mixture compound library may be done using mass spectrometry and NMR by those skilled in the art of structural determination, see for example: Holzgrabe, U. et al., NMR spectroscopy in drug development and analysis, Wiley-VCH, 1999; Weinheim. Wanner, K. et al., Mass Spectrometry in Medicinal Chemistry: Applications in Drug Discovery, Volume 36, Wiley Interscience 2007; Desiderio, D. M. and Nibbering, N. M. "Mass Spectrometry: Instrumentation, Interpretation, and Applications" Wiley Interscience, 2008, ISBN: 0471713953; McLafferty, F. W. and Tureek, F. "Interpretation of Mass Spectra" 4th edition, University Scinece Books, 1993. High resolution mass spectrometry measurement may provide information about the formula of the compound. Tandem mass spectrometry (MS/MS) experiments may provide information about the arrangement and connection of atoms and functional groups in the molecule. NMR spectroscopy analysis may also provide the detailed structure information including the arrangement and connection of atoms and functional groups in the molecule. The structure determination of compounds from the mixture compound library is also aided by the available information that the compounds are derived from erlotinib through known structural modification reactions.

In vitro bioassays. In vitro bioassays are done to measure biological activity of the compounds identified from the mixture compound library in this invention. The types of bioassays and the procedure may be found in the literature for erlotinib or similar drugs produced for treating cancer against EGFR protein, for example: Alexander J. Bridges, et al. J. Med. Chem. 1996, 39, 267-276; Denny, W A, et al. Clinical and Experimental Pharmacology and Physiology 23(5), 424-427, 1996; Rewcastle G W, et al. J Med Chem. 1995; 38(18): 3482-7.

Enzymatic assay. The purified compounds or compound mixtures were tested. EGFR kinase enzymatic activity assay was conducted using HTRF fluorescence detection. HTRF KinEASET™-TK was from Cisbio. EGFR recombinant protein was from Invitrogen. Staurosporine and other reagents and buffers were from Sigma. Compounds were pre-incubated (10 min at room temperature) with EGFR enzyme in reaction buffer in a 384-well plate. Then TK-subatrate and ATP were added in the mixture to start the reaction. After 15-min reaction, Sa-XL665 and TK Ab-Cryptate were added into the wells to stop the reaction. The 384-well plates (black, Corning) were sealed and incubated at RT for 1 h. And measured the fluorescence at 620 nm (Cryptate) and 665 nm (XL665). Each concentration was tested in duplicate wells. EGFR without compound was used as control. Inhibition was calculated as percentage of the EGFR activity (without compound). The fluorescence is measured at 620 nm (Cryptate) and 665 nm (XL665). A ratio is calculated (665/620) for each well. Results are expressed as follows: Specific signal=Ratio (Sample)−Ratio (Negative control).

Cell based EGFR kinase enzymatic activity assay was done using cell proliferation assay of A431 cell lines. A431 cell line was from ATCC (Rockville, Md., USA). The detection was done using CCK-8 cell proliferation assay kit (Dojindo Molecular Technologies, Cell Counting Kit-8). Reaction system consisted of 100 ul cell line solution, using 1 ul stock solution of test compounds. Cell suspension (100 µl/well) was inoculated in a 96-well plate. Microplate was pre-incubated in a humidified incubator (37° C., 5% CO2). 10 µl of the CCK-8 solution was added to each well of the plate. Plates were incubated for 1-4 hours in the incubator. Absorbance at 450 nm was measured using a microplate reader.

In vivo evaluation of antitumor effects of compounds. Evaluation of the compounds of the invention for antitumor effect using animal models may be done by procedures found in the literature for erlotinib or similar drugs produced for treating cancer against EGFR protein, for example: Lu, Y.-Y., et al. "Anti-tumor activity of erlotinib in the BxPC-3 pancreatic cancer cell line" World J Gastroenterol 2008, 14(35): 5403-5411. Ouchi K F, et al., "Antitumor activity of erlotinib in combination with capecitabine in human tumor xenograft models." Cancer Chemother Pharmacol. 2006, 57(5): 693-702. Higgins B, et al., "Antitumor activity of erlotinib (OSI-774, Tarceva) alone or in combination in human non-small cell lung cancer tumor xenograft models." Anticancer Drugs. 2004, (5):503-12. Friess, T. et al., "Combination Treatment with Erlotinib and Pertuzumab against Human Tumor Xenografts Is Superior to Monotherapy." Clin Cancer Res, 2005 11; 5300. SCID nu/nu mice (6-8 weeks old) are injected subcutaneously into the flank at 1×10 6 cells with human A431 and Calu-3 cell lines. The mice are dosed i.p., i.v. or p.o. at 30, 50, 100, 200 mg/kg beginning on approximately day 10, when tumor size is between 50-100 mg. Animals are dosed for 14 consecutive days once a day; tumor size was monitored with calipers twice a week. From the foregoing description, one skilled in the art can easily ascertain the essential characteristics of this invention and, without departing from the spirit and scope thereof, can make various changes and modifications of the invention to adapt it to various usages and conditions.

Exemplary MS or LC-MS Protocol. Samples are analyzed by mass spectrometry alone or by liquid chromatography coupled to mass spectrometry, or other analytical techniques such as NMR, for the quantity and identity of components of the mixture compound libraries described in this method.

Mass spectrometry: Analysis may be performed on, e.g., time-of-flight mass spectrometers LCT (Waters Corporation, Milford, Mass., USA) using a Z-spray (electrospray) ionization source. The electrospray voltage is generally maintained in the range of about 3.5-4.0 kV. Ion optics settings are optimized on the day of the analysis to provide the maximum efficiency of ion to the detector. The effective mass range is generally from m/z 100 to m/z 1000 at a rate of about 1 s/scan.

Liquid chromatography: For example, samples can be introduced through an Agilent1200 (Agilent Technologies, Santa Clara, Calif., USA) chromatography operating in the gradient mode at a flow rate of 1 ml/min. An Eclips C18 base-deactivated column (4.6 mm×150 mm) from Agilent is used for sample separation. The mobile phase gradient is H2O+ACN 90/10 (v/v) containing 0.1% formic acid to a H2O+ACN 10/90 (v/v) containing 0.1% formic acid in 10 minutes. Samples are introduced through an autosampler as part of the Agilent 1200. The sample injection volumes are generally 1-20 μL.

NMR: 1H NMR and 13C NMR spectra were recorded on Varian Inova 400 MHz NMR spectrometer. Chemical shifts are given in parts per million (ppm) using tetramethylsilane as the internal standard for spectra obtained in DMSO-d6, CD3OD, and CDCl3.

Compound synthesis. The specific approaches and compounds shown below are not intended to be limiting. The suitability of a chemical group in a compound structure for use in the synthesis of another compound is within the knowledge of one of ordinary skill in the art. Additional methods of synthesizing compounds of Formula I-III and their synthetic precursors, including those within routes not explicitly shown in schemes herein, are within the means of chemists of ordinary skill in the art.

Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene T W et al., Protective Groups in Organic Synthesis, 3rd Ed., John Wiley and Sons (1999); Fieser L et al., Fieser and Fieser's Reagents for Organic Synthesis, John Wiley and Sons (1994); and. Paquette L, ed., Encyclopedia of Reagents for Organic Synthesis, John Wiley and Sons (1995); Corey, E. J. and Cheng, X. -M., The Logic of Chemical Synthesis, Wiley, New York, 1989, and subsequent editions thereof.

Scheme 1 shows a general route to prepare compounds of Formula I-III by those skilled in the art of organic synthesis, Ra and Rb represent substitution groups that are stable in the shown synthetic step.

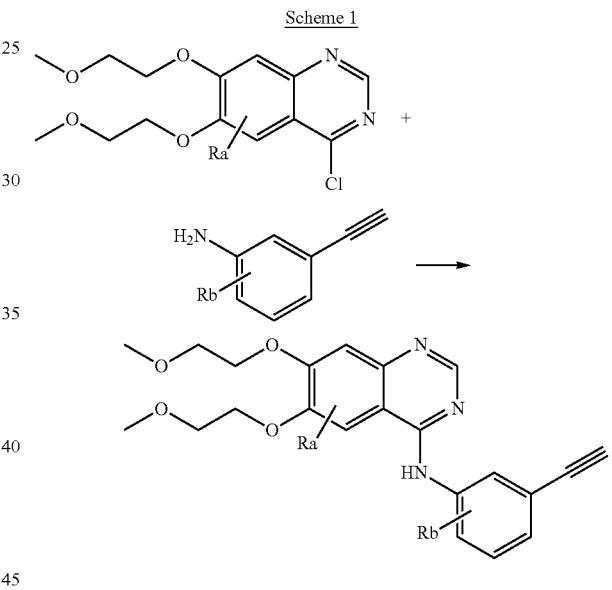

Example of synthetic procedure for a representative compound of this invention is show below.

Synthesis of N-(5-ethynyl-2-fluorophenyl)-6,7-bis(2-methoxyethoxy)quinazolin-4-amine (Scheme 2)

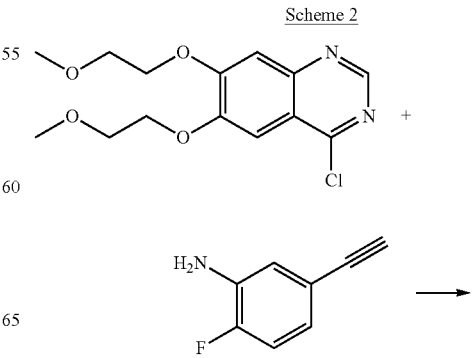

-continued

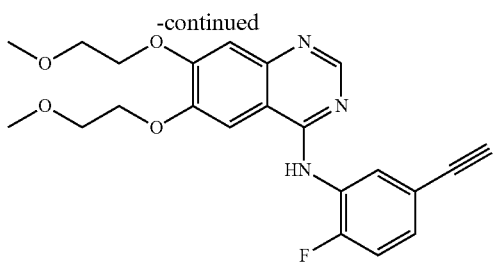

4-Chloro-6,7-bis(2-methoxyethoxy)quinazoline (140 mg, 0.447 mmol) and 5-ethynyl-2-fluoroaniline (66 mg, 0.489 mmol) were reacted in refluxing isopropanol (3 mL) overnight under an atmosphere of N2. The solvent was removed by rotary evaporation and the residue was dissolved in CHCl3 and then treated with saturated aqueous NaHCO3. The organic layer was separated and washed with brine, dried over Na2SO4, filtered and concentrated in vacuo. The crude product was chromatographed on silica using 40% acetone/CH2Cl2 to provide 116 mg of the pure title product as its free base. This oil was dissolved in a minimum volume of CHCl3, diluted with several volumes of ether and titrated with 1M HCl in ether to precipitate the title product as a white solid (99 mg; 54%; LC-MS: m/z=412.1664, m/z(calc)=412.1667).

EXAMPLES

The following examples are offered to illustrate, but not to limit the claims. One of ordinary skill in the art will recognize a variety of non-critical parameters that may be altered without departing from the scope of the claims.

Example 1

N-(3-ethynyl-5-fluorophenyl)-6,7-bis(2-methoxyethoxy)quinazolin-4-amine

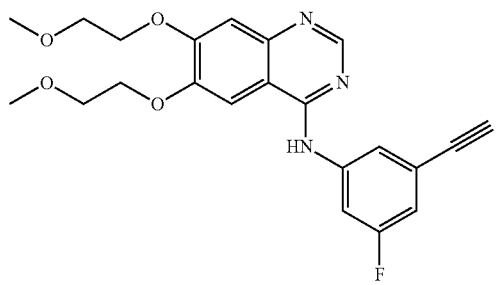 [SMILES: C#Cc1cc(F)cc(Nc2ncnc3cc(OCCOC)c(OCCOC)cc23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-fluorinated erlotinib was isolated and purified by successive preparative HPLC separations. The purified compound was analyzed by LC-MS/MS and NMR to provide the structure of the title compound. The observed m/z value 412.1665 (Thermo Finnigan LTQ Orbitrap, positive ion mode), is consistent with calculated m/z of protonated mono-fluorinated erlotinib (m/z (calc)=412.1667), molecular formula: C22H23FN3O4+. High resolution MSn (n=2-4) experiments on LTQ orbitrap indicate the fluorine substitution is on the 3-ethynylphenyl ring of erlotinib (fragment at m/z 136.0555, calc: 136.0557 for C8H7FN+). 1H-NMR spectra data indicate the fluorine substitution is at the 5-position of the 3-ethynylphenyl ring of erlotinib. 1H-NMR (400 MHz, DMSO-d6) δ ppm 3.42 (s, 3H), 3.45 (s, 3H), 3.83 (m, 4H), 4.2-4.4 (m, 5H), 7.06 (dt, J=8.1, 1.7, 1H), 7.49 (s, 1H), 7.74 (dt, J=8.0, 1.5, 1H), 8.01 (t, 1.6, 1H), 8.21 (s, 1H), 9.02 (s, 1H).

Example 2

N-(5-ethynyl-2-fluorophenyl)-6,7-bis(2-methoxyethoxy)quinazolin-4-amine

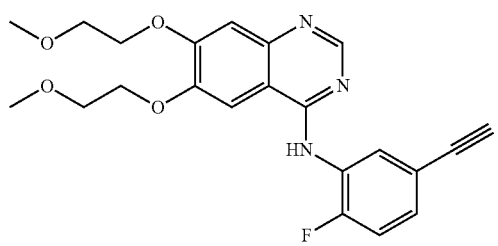 [SMILES: C#Cc1ccc(F)c(Nc2ncnc3cc(OCCOC)c(OCCOC)cc23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-fluorinated erlotinib was isolated and purified by successive preparative HPLC separations. The purified compound was analyzed by LC-MS/MS and NMR to provide the structure of the title compound. The observed m/z value 412.1664 (Thermo Finnigan LTQ Orbitrap, positive ion mode), is consistent with calculated m/z of protonated mono-fluorinated erlotinib (m/z (calc)=412.1667), molecular formula: C22H23FN3O4+. High resolution MSn (n=2-4) experiments on LTQ orbitrap indicate the fluorine substitution is on the 3-ethynylphenyl ring of erlotinib (fragment at m/z 136.0556, calc: 136.0557 for C8H7FN+). 1H-NMR spectra data indicate the fluorine substitution is at the 6-position of the 3-ethynylphenyl ring of erlotinib. 1H-NMR (400 MHz, DMSO-d6) δ ppm 3.43 (s, 3H), 3.46 (s, 3H), 3.8 (m, 4H), 4.4 (m, 5H), 7.29 (s, 1H), 7.42

(dd, J=8.4, 1.9, 1H), 7.56 (dd, 8.4, 8.0, 1H), 8.36 (dd, J=4.8, 1.9, 1H), 8.49 (s, 1H), 8.84 (s, 1H).

Example 3

N-(5-ethynyl-2-chlorophenyl)-6,7-bis(2-methoxyethoxy)quinazolin-4-amine

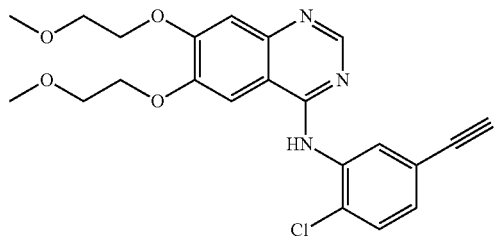 [SMILES: C#Cc1ccc(Cl)c(Nc2ncnc3cc(OCCOC)c(OCCOC)cc23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-chlorinated erlotinib was isolated and purified by successive preparative HPLC separations. The purified compound was analyzed by LC-MS/MS and NMR to provide the structure of the title compound. The observed m/z value 428.1371 (Thermo Finnigan LTQ Orbitrap, positive ion mode), is consistent with calculated m/z of protonated mono-chlorinated erlotinib (m/z (calc)=428.1372), molecular formula: C22H23ClN3O4+. High resolution MSn (n=2-4) experiments on LTQ orbitrap indicate the fluorine substitution is on the 3-ethynylphenyl ring of erlotinib (fragment at m/z 152.0262, calc: 152.0261 for C8H7ClN+). 1H-NMR spectra data indicate the chlorine substitution is at the 6-position of the 3-ethynylphenyl ring of erlotinib. 1H-NMR (400 MHz, DMSO-d6) δ ppm 3.36 (s, 3H), 3.38 (s, 3H), 3.88 (m, 4H), 4.3-4.4 (m, 5H), 7.38 (s, 1H), 7.46 (dd, J=8.6, 2.7, 1H), 7.87 (d, J=8.6, 1H), 7.96 (d, J=2.7, 1H), 8.53 (s, 1H), 8.87 (s, 1H).

Example 4

N-(3-ethynyl-4-chlorophenyl)-6,7-bis(2-methoxyethoxy)quinazolin-4-amine

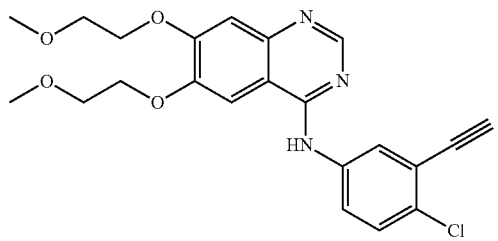 [SMILES: C#Cc1cc(Nc2ncnc3cc(OCCOC)c(OCCOC)cc23)ccc1Cl]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-chlorinated erlotinib was isolated and purified by successive preparative HPLC separations. The purified compound was analyzed by LC-MS/MS and NMR to provide the structure of the title compound. The observed m/z value 428.1374 (Thermo Finnigan LTQ Orbitrap, positive ion mode), is consistent with calculated m/z of protonated mono-chlorinated erlotinib (m/z (calc)=428.1372), molecular formula: C22H23ClN3O4+. High resolution MSn (n=2-4) experiments on LTQ orbitrap indicate the fluorine substitution is on the 3-ethynylphenyl ring (or ethynyl group) of erlotinib (fragment at m/z 152.0259, calc: 152.0261 for C8H7ClN+). 1H-NMR spectra data indicate the chlorine substitution is at the 4-position of the 3-ethynylphenyl ring of erlotinib. 1H-NMR (400 MHz, DMSO-d6) δ ppm 3.36 (s, 6H), 3.78 (m, 4H), 4.36 (m, 4H), 4.68 (s, 1H), 7.39 (s, 1H), 7.66 (d, J=8.8, 1H), 7.86 (dd, J=8.8, 2.4, 1H), 8.06 (d, J=2.4, 1H), 8.46, (s, 1H), 8.89 (s, 1H).

Example 5

N-(3-ethynylphenyl)-5,8-difluoro-6,7-bis(2-methoxyethoxy)quinazolin-4-amine

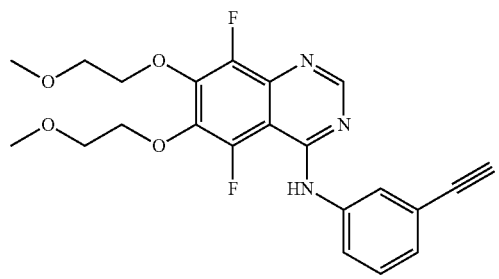 [SMILES: C#Cc1cccc(Nc2ncnc3c(F)c(OCCOC)c(OCCOC)c(F)c23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to di-fluorinated erlotinib was isolated and purified by successive preparative HPLC separations. The purified compound was analyzed by LC-MS/MS and NMR to provide the structure of the title compound. The observed m/z value 430.1570 (Thermo Finnigan LTQ Orbitrap, positive ion mode), is consistent with calculated m/z of protonated di-fluorinated erlotinib (m/z (calc)=430.1573), molecular formula: C22H22F2N3O4+. High resolution MSn (n=2-4) experiments on LTQ orbitrap indicate both fluorine substitutions are on the quinazoline ring side of erlotinib (fragment at m/z 118.0649, calc: 118.0651 for C8H8N+ indicates the 3-ethynylphenyl ring is not substituted) and are not on the side chain of the quinazoline ring (elimination of two C3H6O groups observed from the side chains). 1H-NMR spectra data indicate the fluorine substitutions are at the 5 and 8-position of the quinazoline ring of erlotinib. 1H-NMR (400 MHz, DMSO-d6) δ ppm 3.39 (s, 6H), 3.74 (m, 4H), 4.23 (s, 1H), 4.35 (m, 4H), 7.44 (m, 2H), 7.97 (dd, J=8.3, 1.9, 1H), 8.17 (dd, J=2.4, 1.9, 1H), 9.00 (s, 1H).

Example 6

N-(3-ethynylphenyl)-5,8-difluoro-6,7-bis(2-methoxyethoxy)-5,8-dihydroquinazolin-4-amine

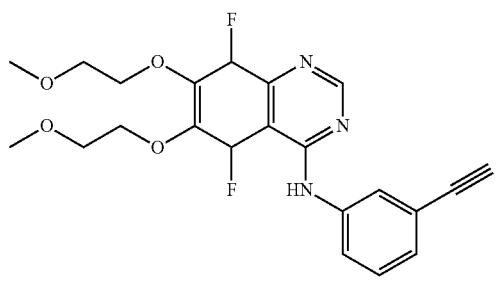 [SMILES: C#Cc1cccc(Nc2ncnc3c2C(F)C(OCCOC)=C(OCCOC)C3F)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to addition of fluorine molecule (F2) to erlotinib was isolated and purified by successive preparative HPLC separations. The purified compound was analyzed by LC-MS/MS and NMR to provide the structure of the title compound. The observed m/z value 432.1726 (Thermo Finnigan LTQ Orbitrap, positive ion mode), is consistent with calculated m/z of protonated erlotinib with fluorine molecule (F2) addition (m/z (calc)=432.1729), molecular formula: C22H24F2N3O4+. High resolution MSn (n=2-4) experiments on LTQ orbitrap indicate both fluorine substitutions are on the quinazoline ring side of erlotinib (fragment at m/z 118.0649, calc: 118.0651 for C8H8N+ indicates the 3-ethynylphenyl ring is not substituted) and are not on the side chain of the quinazoline ring (elimination of two C3H6O groups observed from the side chains). 1H-NMR spectra data indicate the fluorine molecule (F2) addition is to the 5 and 8-position of the quinazoline ring of erlotinib. 1H-NMR (400 MHz, DMSO-d6) δ ppm 3.30 (s, 3H), 3.42 (s, 3H), 3.82 (m, 4H), 4.22 (s, 1H), 4.34 (m, 4H), 5.57 (d, J=8.2, 1H), 5.83 (d, J=8.3, 1H), 7.40 (dt, J=8.0, 1.8, 1H), 7.64 (ddd, J=8.3, 8.0, 1.9, 1H), 7.92 (dt, J=8.3, 1.8, 1H), 8.06 (t, J=1.9, 1H), 8.68 (s, 1H).

Example 7

N-(3-ethynylphenyl)-5-fluoro-6,7-bis(2-methoxyethoxy)quinazolin-4-amine

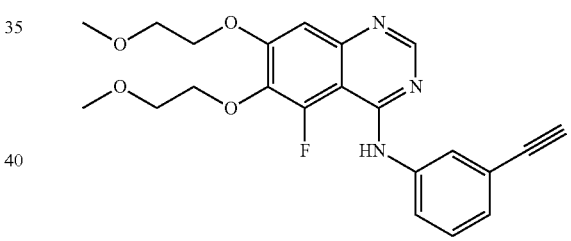

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-fluorinated erlotinib was isolated and purified by successive preparative HPLC separations. The purified compound was analyzed by LC-MS/MS and NMR to provide the structure of the title compound. The observed m/z value 412.1667 (Thermo Finnigan LTQ Orbitrap, positive ion mode), is consistent with calculated m/z of protonated mono-fluorinated erlotinib (m/z (calc)=412.1667), molecular formula: C22H23FN3O4+. High resolution MSn (n=2-4) experiments on LTQ orbitrap indicate the fluorine substitution is on the quinazoline ring side of erlotinib (fragment at m/z 118.0649, calc: 118.0651 for C8H8N+ indicates the 3-ethynylphenyl ring is not substituted) and are not on the side chain of the quinazoline ring (elimination of two C3H6O groups observed from the side chains). 1H-NMR spectra data indicate the fluorine substitution is at the 5-position of the quinazoline ring of erlotinib. 1H-NMR (400 MHz, DMSO-d6) δ ppm 3.45 (s, 6H), 3.79 (m, 4H), 4.30 (m, 3H), 4.39 (t, J=7.2, 2H), 7.13 (s, 1H), 7.41 (ddd, J=8.3, 2.4, 1.3, 1H), 7.80 (m, 2H), 7.92 (ddd, J=8.3, 1.8, 1.3, 1H), 9.09 (s, 1H).

Example 8

N-(3-ethynylphenyl)-5-chloro-6,7-bis(2-methoxyethoxy)quinazolin-4-amine

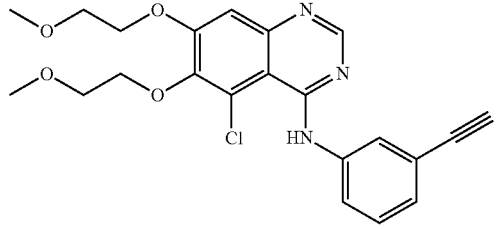 [SMILES: C#Cc1cccc(Nc2ncnc3cc(OCCOC)c(OCCOC)c(F)c23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-chlorinated erlotinib was isolated and purified by successive preparative HPLC separations. The purified compound was analyzed by LC-MS/MS and NMR to provide the structure of the title compound. The observed m/z value 428.1370 (Thermo Finnigan LTQ Orbitrap, positive ion mode), is consistent with calculated m/z of protonated mono-chlorinated erlotinib (m/z (calc)=428.1372), molecular formula: C22H23ClN3O4+. High resolution MSn (n=2-4) experiments on LTQ orbitrap indicate the fluorine substitution is on the quinazoline ring of erlotinib (fragment at m/z 118.0649, calc: 118.0651 for C8H8N+ indicates the 3-ethynylphenyl ring is not substituted) and are not on the side chain of the quinazoline ring (elimination of two C3H6O groups from the side chains). 1H-NMR spectra data indicate the chlorine substitution is at the 5-position of the quinazoline ring of erlotinib. 1H-NMR (400 MHz, DMSO-d6) δ ppm 3.42 (s, 3H), 3.46 (s, 3H), 3.83 (m, 4H), 4.27 (s, 1H), 4.36 (m, 4H), 7.39 (s, 1H), 7.49 (dd, J=8.5, 8.3, 1H), 7.66 (ddd, J=8.5, 2.5, 2.2, 1H), 7.87 (dd, J=2.5, 1.8, 1H), 7.91 (ddd, J=8.3, 2.2, 1.8), 8.93 (s, 1H).

Example 9

N-(3-ethynylphenyl)-8-fluoro-6,7-bis(2-methoxyethoxy)quinazolin-4-amine

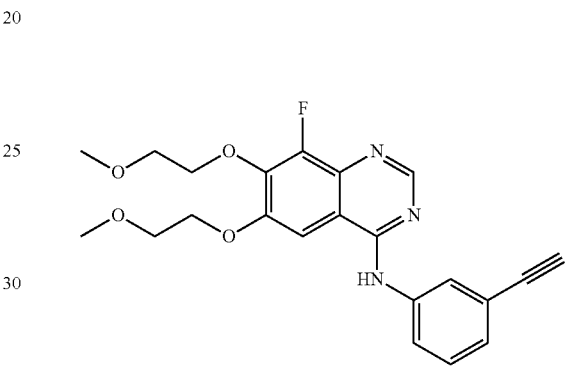

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-fluorinated erlotinib was isolated and purified by successive preparative HPLC separations. The purified compound was analyzed by LC-MS/MS and NMR to provide the structure of the title compound. The observed m/z value 412.1668 (Thermo Finnigan LTQ Orbitrap, positive ion mode), is consistent with calculated m/z of protonated mono-fluorinated erlotinib (m/z (calc)=412.1667), molecular formula: C22H23FN3O4+. High resolution MSn (n=2-4) experiments on LTQ orbitrap indicate the fluorine substitution is on the quinazoline ring side of erlotinib (fragment at m/z 118.0649, calc: 118.0651 for C8H8N+ indicates the 3-ethynylphenyl ring is not substituted) and are not on the side chain of the quinazoline ring (elimination of two C3H6O groups from the side chains). 1H-NMR spectra data indicate the fluorine substitution is at the 8-position of the quinazoline ring of erlotinib. 1H-NMR (400 MHz, DMSO-d6) δ ppm 3.45 (s, 6H), 3.76 (m, 4H), 4.30 (s, 1H), 4.38 (m, 4H), 7.61 (m, 2H), 8.0 5 (m, 2H), 8.41 (s, 1H), 8.89 (s, 1H).

Example 10

N-(3-ethynylphenyl)-5,6,7,8-tetrafluoro-6,7-bis(2-methoxyethoxy)-5,6,7,8-tetrahydroquinazolin-4-amine

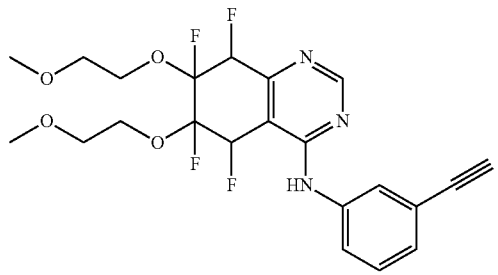 [SMILES: C#Cc1cccc(Nc2ncnc3c2C(F)C(F)(OCCOC)C(F)(OCCOC)C3F)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to addition of 2 fluorine molecules (2F2) to erlotinib was isolated and purified by successive preparative HPLC separations. The purified compound was analyzed by LC-MS/MS and NMR to provide the structure of the title compound. The observed m/z value 466.1385 (Thermo Finnigan LTQ Orbitrap, positive ion mode), is consistent with calculated m/z of protonated erlotinib with addition of 2 fluorine molecules (2F2) (m/z(calc) =466.1384), molecular formula: C22H24O4N3F2+. High resolution MSn (n=2-4) experiments on LTQ orbitrap indicate the 4 fluorine atoms are added to the quinazoline ring side of erlotinib (fragment at m/z 118.0649, calc: 118.0651 for C8H8N+ indicates the 3-ethynylphenyl ring is not substituted) and are not on the side chain of the quinazoline ring (elimination of two C3H6O groups from the side chains). 1H-NMR spectra data indicate the fluorine addition is to the 5, 6, 7 and 8-positions of the quinazoline ring of erlotinib. 1H-NMR (400 MHz, DMSO-d6) δ ppm 3.41 (s, 6H), 3.72 (t, J=5.2, 2H), 3.84 (t, J=5.2, 2H), 4.33 (m, 3H), 4.45 (t, J=4.6, 2H), 5.20 (d, J=8.2, 1H), 5.59 (d, J=8.3, 1H), 7.32 (ddd, J=8.3, 2.2, 1.4, 1H), 7.66 (dd, J=8.3, 8.0, 1H), 7.79 (ddd, J=8.0, 1.8, 1.4, 1H), 7.93 (dd, J=2.2, 1.8, 1H), 8.49 (s, 1H).

Example 11

N-(3-ethynyl-4-fluorophenyl)-5-fluoro-6,7-bis(2-methoxyethoxy)quinazolin-4-amine

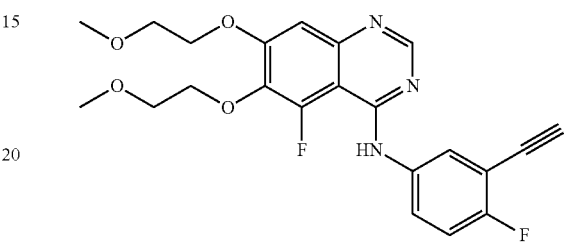

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to di-fluorinated erlotinib was isolated and purified by successive preparative HPLC separations. The purified compound was analyzed by LC-MS/MS and NMR to provide the structure of the title compound. The observed m/z value 430.1574 (Thermo Finnigan LTQ Orbitrap, positive ion mode), is consistent with calculated m/z of protonated di-fluorinated erlotinib (m/z (calc)=430.1573), molecular formula: C22H22F2N3O4+. High resolution MSn (n=2-4) experiments on LTQ orbitrap indicate one fluorine substitutions are at the 3-ethynylphenyl ring side and one fluorine substitution is at the quinazoline ring side of erlotinib (fragment at m/z 136.0558, calc: 136.0557 for C8H7FN+). 1H-NMR spectra data indicate the fluorine substitutions are at the 4-position of the 3-ethynylphenyl ring and 5-position of the quinazoline ring of erlotinib. 1H-NMR (400 MHz, DMSO-d6) δ ppm 3.33 (s, 3H), 3.38 (s, 3H), 3.82 (m, 4H), 4.31 (s, 1H), 4.41 (m, 4H), 7.29 (s, 1H), 7.38 (dd, J=8.6, 8.2, 1H), 7.67 (ddd, J=8.2, 5.1, 1.8, 1H), 8.12 (dd, J=5.3, 1.8, 1H), 8.74 (s, 1H).

Example 12

N-(3-ethynyl-4-chlorophenyl)-5-fluoro-6,7-bis(2-methoxyethoxy)quinazolin-4-amine

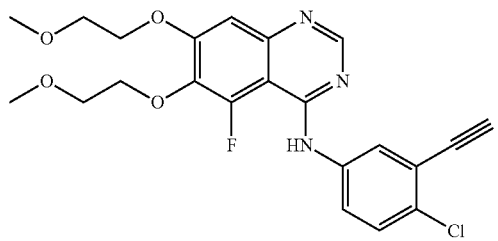 [SMILES: C#Cc1cc(Nc2ncnc3cc(OCCOC)c(OCCOC)c(F)c23)ccc1F]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to substitution of erlotinib by one fluorine and one chlorine was isolated and purified by successive preparative HPLC separations. The purified compound was analyzed by LC-MS/MS and NMR to provide the structure of the title compound. The observed m/z value 446.1273 (Thermo Finnigan LTQ Orbitrap, positive ion mode), is consistent with calculated m/z of protonated erlotinib with one fluorine and one chlorine substitution (m/z (calc)=446.1277), molecular formula: C22H22ClFN3O4+. High resolution MSn (n=2-4) experiments on LTQ orbitrap indicate chlorine substitution is on the 3-ethynylphenyl ring and fluorine substitution is on the quinazoline ring of erlotinib (fragment at m/z 152.0259, calc: 152.0261 for C8H7ClN+). 1H-NMR spectra data indicate the chlorine substitutions is at the 4-position of 3-ethynylphenyl ring and fluorine substitution is at 5-position of the quinazoline ring of erlotinib. 1H-NMR (400 MHz, DMSO-d6) δ ppm 3.44 (s, 6H), 3.79 (m, 4H), 4.25 (s, 1H), 4.31 (t, J=4.2, 2H), 4.4.3 (t, J=4.2, 2H), 7.21 (s, 1H), 7.61 (d, J=8.6, 1H), 7.86 (dd, J=8.6, 2.4, 1H), 7.97 (d, J=2.4, 1H), 9.05 (s, 1H).

Example 13

N-(5-ethynyl-2-fluorophenyl)-5-fluoro-6,7-bis(2-methoxyethoxy)quinazolin-4-amine

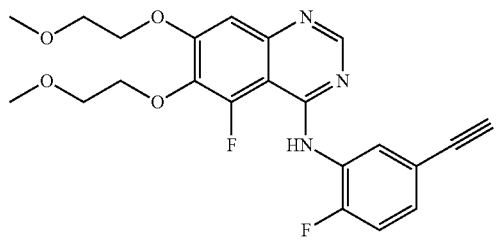 [SMILES: C#Cc1ccc(F)c(Nc2ncnc3cc(OCCOC)c(OCCOC)c(F)c23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to di-fluorinated erlotinib was isolated and purified by successive preparative HPLC separations. The purified compound was analyzed by LC-MS/MS and NMR to provide the structure of the title compound. The observed m/z value 430.1575 (Thermo Finnigan LTQ Orbitrap, positive ion mode), is consistent with calculated m/z of protonated di-fluorinated erlotinib (m/z (calc)=430.1573), molecular formula: C22H22O4N3F2+. High resolution MSn (n=2-4) experiments on LTQ orbitrap indicate one fluorine substitutions are at the 3-ethynylphenyl ring side and one fluorine substitution is at the quinazoline ring side of erlotinib (fragment at m/z 136.0554, calc: 136.0557 for C8H7FN+). 1H-NMR spectra data indicate the fluorine substitutions are at the 6-position of 3-ethynylphenyl ring and 5-position of the quinazoline ring of erlotinib. 1H-NMR (400 MHz, DMSO-d6) δ ppm 3.31 (s, 3H), 3.39 (s, 3H), 3.71 (m, 4H), 4.22 (s, 1H), 4.36 (m, 4H), 7.19 (s, 1H), 7.28 (ddd, J=8.0, 5.0, 1.9, 1H), 7.62 (dd, J=8.5, 8.0, 1H), 8.37 (dd, J=5.2, 1.8, 1H), 9.02 (s, 1H).

Example 14

N-(5-ethynyl-2-fluorophenyl)-5-chloro-6,7-bis(2-methoxyethoxy)quinazolin-4-amine

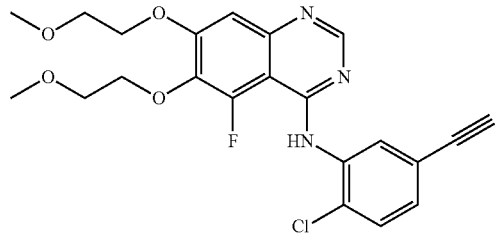 [SMILES: C#Cc1ccc(Cl)c(Nc2ncnc3cc(OCCOC)c(OCCOC)c(F)c23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to substitution of erlotinib by one fluorine and one chlorine was isolated and purified by successive preparative HPLC separations. The purified compound was analyzed by LC-MS/MS and NMR to provide the structure of the title compound. The observed m/z value 446.1277 (Thermo Finnigan LTQ Orbitrap, positive ion mode), is consistent with calculated m/z of protonated erlotinib with one fluorine and one chlorine substitution (m/z (calc)=446.1277), molecular formula: C22H22ClFN3O4+. High resolution MSn (n=2-4) experiments on LTQ orbitrap indicate chlorine substitution is on the 3-ethynylphenyl ring and fluorine substitution is on the quinazoline ring of erlotinib (fragment at m/z 152.0258, calc: 152.0261 for C8H7ClN+). 1H-NMR spectra data indicate the chlorine substitutions is at 6-position of 3-ethynylphenyl ring and fluorine substitution is at 5-position of the quinazoline ring of erlotinib. 1H-NMR (400 MHz, DMSO-d6) δ ppm 3.18 (s, 3H), 3.40 (s, 6H), 3.52 (s, 1H), 3.78 (t, J=4.2, 2H), 3.87 (t, J=4.2, 2H), 4.31 (m, 5H), 7.20 (dd, J=8.6, 1.9, 1H), 7.29 (s, 1H), 7.66 (d, J=8.6, 1H), 7.87 (d, J=1.9, 1H), 8.92 (s, 1H).

Example 15

N-(3-ethynylphenyl)-2-fluoro-6,7-bis(2-methoxyethoxy)quinazolin-4-amine

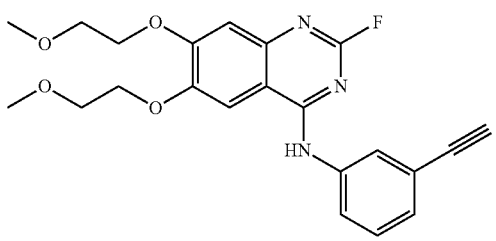 [SMILES: C#Cc1cccc(Nc2nc(F)nc3cc(OCCOC)c(OCCOC)cc23)c1]

300 mg erlotinib was dissolved in 200 mL CH2Cl2 at −78° C. cooled by dry-ice/acetone bath. A mixture of F2 and N2 gas containing 20% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-fluorinated erlotinib was isolated and purified by successive preparative HPLC separations. The purified compound was analyzed by LC-MS/MS and NMR to provide the structure of the title compound. The observed m/z value 412.1665 (Thermo Finnigan LTQ Orbitrap, positive ion mode), is consistent with calculated m/z of protonated mono-fluorinated erlotinib (m/z (calc)=412.1667), molecular formula: C22H23FN3O4+. High resolution MSn (n=2-4) experiments on LTQ orbitrap indicate the fluorine substitution is on the quinazoline ring side of erlotinib (fragment at m/z 118.0650, calc: 118.0651 for C8H8N+ indicates the 3-ethynylphenyl ring is not substituted) and are not on the side chain of the quinazoline ring (elimination of two C3H6O groups from the side chains). 1H-NMR spectra data indicate the fluorine substitution is at the 2-position of the quinazoline ring of erlotinib (low field proton signal at close to 9 ppm disappeared). 1H-NMR (400 MHz, DMSO-d6) δ ppm 3.34 (s, 6H), 3.71 (t, J=4.2, 2H), 3.83 (t, J=4.2, 2H), 4.25 (s, 1H), 4.34 (t, J=4.3, 2H), 4.38 (t, J=4.3, 2S), 7.33 (s, 1H), 7.57 (dd, J=8.5, 8.2, 1H), 7.71 (ddd, J=8.5, 2.4, 1.9, 1H), 7.80 (ddd, J=8.2, 2.2, 1.9, 1H), 8.09 (dd, J=2.2, 2.4, 1H), 8.43 (s, 1H).

Example 16

N-(3-(fluoroethynyl)phenyl)-6,7-bis(2-methoxyethoxy)quinazolin-4-amine

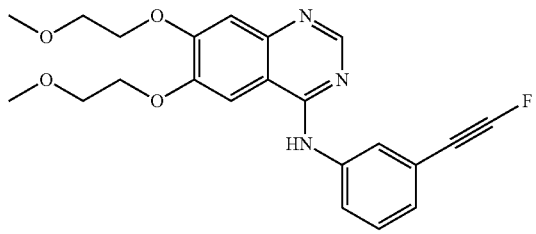 [SMILES: COCCOc1cc2ncnc(Nc3cccc(C#CF)c3)c2cc1OCCOC]

300 mg erlotinib was dissolved in 200 mL CH2Cl2 at −78° C. cooled by dry-ice/acetone bath. A mixture of F2 and N2 gas containing 10% F2/80% N2 was passed through the reaction vessel continuously at a flow rate of 2 L/min. Reaction was stopped after 30 min and the solvent was removed under vacuum. Dried reaction products were dissolved in 3 mL acetonitrile and was separated on an Agilent Zorbax C8 250× 4.6 mm column, gradient elution from 30% MeOH/70% 0.1% formic acid in dd-H2O to 90% MeOH/10% 0.1% formic acid in dd-H2O, 1 ml/min total flow rate. Each fraction was analyzed by mass spectrometry. Fractions containing reaction products without excess amount of the starting material erlotinib, were mixed to form the modified erlotinib mixture compound library for drug property screening to identify components with improved properties over erlotinib. A component with m/z value corresponding to mono-fluorinated erlotinib was isolated and purified by successive preparative HPLC separations. The purified compound was analyzed by LC-MS/MS and NMR to provide the structure of the title compound. The observed m/z value 412.1668 (Thermo Finnigan LTQ Orbitrap, positive ion mode), is consistent with calculated m/z of protonated mono-fluorinated erlotinib (m/z (calc)=412.1667), molecular formula: C22H23FN3O4+. High resolution MSn (n=2-4) experiments on LTQ orbitrap indicate the fluorine substitution is on the 3-ethynylphenyl ring of erlotinib (fragment at m/z 136.0554, calc: 136.0557 for C8H7FN+). 1H-NMR spectra data indicate the fluorine substitution is at the terminal position of the ethynyl group of erlotinib (high field proton signal at around 3 ppm disappeared). 1H-NMR (400 MHz, DMSO-d6) δ ppm 3.34 (s, 3H), 3.39 (s, 3H), 3.75 (t, J=4.2, 2H), 3.84 (t, J=4.2, 2H), 4.37 (m, 4H), 7.36 (s, 1H), 7.42 (ddd, J=8.6, 1.9, 1.3, 1H), 7.51 (dd, J=8.6, 8.0, 1H), 7.78 (ddd, J=8.0, 1.9, 1.6, 1H), 8.19 (dd, J=1.6, 1.3, 1H), 8.58 (s, 1H), 8.69 (s, 1H).

REFERENCES CITED

US Patent Documents

Cheng, X. U.S. patent application Ser. No. 12/946,533—Method for improving the properties of a drug lead compound, US patent application on November, 2010, claiming priority benefit of U.S. Provisional Application 61/281,371, filed on November, 2009.

U.S. Pat. No. 5,747,498 Alkynyl and azido-substituted 4-anilinoquiazolines
Schnur, R C et al. May 5, 1998, 653, 786, Schnur, R. C.; Arnold, L. D. WO 9630347
U.S. Pat. No. 4,343,940 A Anti-tumor quinazoline compounds August-1982 544/283
U.S. Pat. No. 5,457,105 A Quinazoline derivatives useful for treatment of neoplastic disease October-1995 514/234.5
U.S. Pat. No. 5,480,883 A Bis mono- and bicyclic aryl and heteroaryl compounds which inhibit EGF and/or PDGF receptor tyrosine kinase January-1996 514/249
Uckun, F M. et al. U.S. Pat. No. 6,552,027—Quinazolines for treating brain tumor US patent Issued on Apr. 22, 2003
Santafianos, D. P.; Norris, T.; Lehner, R. S.; Processes and intermediates for preparing anti-cancer cpds. U.S. Pat. No. 6,476,040
Other Patent Documents
WO 2008012326 2,4-Substituted quinazolines as lipic kinase inhibitors, Jan. 31, 2008, PCT/EP2007/057669, Stauffer, F.
Other References
Sorbera, L. A., Castaner, J., Silvestre, J. S., Bayes, M. Erlotinib Hydrochloride, Drugs of the Future 2002, 27(10): 923.
Denny, W A, et al. Structure-activity relationships for 4-anilinoquinazolines as potent inhibitors a the ATP binding site of the epidermal growth factor receptor in vitro. Clinical and Experimental Pharmacology and Physiology 23(5), 424-427, 1996.
Rewcastle G W, et al. Tyrosine kinase inhibitors. 5. Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. J Med Chem. 1995; 38(18): 3482-7.
Bridges A J, et al. Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor. J Med Chem. 1996; 39(1): 267-76.
Holzgrabe, U. et al., NMR spectroscopy in drug development and analysis, Wiley-VCH, 1999, Weinheim. Lee, M. S. Integrated Strategies for Drug Discovery Using Mass Spectrometry, Wiley-Interscience, 2005.
Wanner, K. et al., Mass Spectrometry in Medicinal Chemistry: Applications in Drug Discovery, Volume 36, Wiley Interscience, 2007.
Desiderio, D. M. and Nibbering, N. M. "Mass Spectrometry: Instrumentation, Interpretation, and Applications" Wiley Interscience, 2008, ISBN: 0471713953.
McLafferty, F. W. and Tureek, F. "Interpretation of Mass Spectra" 4th edition, University Scinece Books, 1993.
Lu, Y.-Y.; et al. "Anti-tumor activity of erlotinib in the BxPC-3 pancreatic cancer cell line" World J Gastroenterol 2008, 14(35): 5403-5411.
Ouchi K F, et al., "Antitumor activity of erlotinib in combination with capecitabine in human tumor xenograft models." Cancer Chemother Pharmacol. 2006, 57(5): 693-702.
Higgins B, et al., "Antitumor activity of erlotinib (OSI-774, Tarceva) alone or in combination in human non-small cell lung cancer tumor xenograft models."
Anticancer Drugs. 2004, (5):503-12.
Friess, T.; et al., "Combination Treatment with Erlotinib and Pertuzumab against Human Tumor Xenografts Is Superior to Monotherapy." Clin Cancer Res 2005 11; 5300.

What is claimed is:

1. A compound isolated from a non-selective reaction product mixture of erlotinib selected from the group cosisting of:

N-(3-ethynyl-5-fluorophenyl)-6,7-bis(2-methoxyethoxy)quinazolin-4-amine;

N-(5-ethynyl-2-fluorophenyl)-6,7-bis(2-methoxyethoxy)quinazolin-4-amine;

N-(5-ethynyl-2-chlorophenyl)-6,7-bis(2-methoxyethoxy)quinazolin-4-amine;

N-(3-ethynyl-4-chlorophenyl)-6,7-bis(2-methoxyethoxy)quinazolin-4-amine;

N-(3-ethynylphenyl)-5,8-difluoro-6,7-bis(2-methoxyethoxy)quinazolin-4-amine;

N-(3-ethynylphenyl)-5,8-difluoro-6,7-bis(2-methoxyethoxy)-5,8-dihydroquinazolin-4-amine;

N-(3-ethynylphenyl)-5-fluoro-6,7-bis(2-methoxyethoxy)quinazolin-4-amine;

N-(3-ethynylphenyl)-5-chloro-6,7-bis(2-methoxyethoxy)quinazolin-4-amine;

N-(3-ethynylphenyl)-8-fluoro-6,7-bis(2-methoxyethoxy)quinazolin-4-amine;

N-(3-ethynylphenyl)-5,6,7,8-tetrafluoro-6,7-bis(2-methoxyethoxy)-5,6,7,8-tetrahydroquinazolin-4-amine;

N-(3-ethynyl-4-fluorophenyl)-5-fluoro-6,7-bis(2-methoxyethoxy)quinazolin-4-amine;

N-(3-ethynyl-4-chlorophenyl)-5-fluoro-6,7-bis(2-methoxyethoxy)quinazolin-4-amine;

N-(5-ethynyl-2-fluorophenyl)-5-fluoro-6,7-bis(2-methoxyethoxy)quinazolin-4-amine; and N-(5-ethynyl-2-fluorophenyl)-5-chloro-6,7-bis(2-methoxyethoxy)quinazolin-4-amine.

\* \* \* \* \*